United States Patent [19]
Diaz et al.

[11] Patent Number: 5,836,946
[45] Date of Patent: Nov. 17, 1998

[54] CATHETER FOR DELIVERY OF ELECTRIC ENERGY AND A PROCESS FOR MANUFACTURING SAME

[75] Inventors: Cesar M. Diaz; Christopher Reiser, both of Colorado Springs, Colo.

[73] Assignee: The Spectranetics Corporation, Colorado Springs, Colo.

[21] Appl. No.: 873,753

[22] Filed: Jun. 12, 1997

Related U.S. Application Data

[63] Continuation-in-part of Ser. No. 662,799, Jun. 12, 1996.
[51] Int. Cl.$^6$ .................................................... A61B 17/36
[52] U.S. Cl. ................................................ 606/45; 606/48
[58] Field of Search ................................... 607/116, 119, 607/122; 606/41, 45, 48, 49, 50

[56] References Cited

U.S. PATENT DOCUMENTS

| | | |
|---|---|---|
| 4,559,951 | 12/1985 | Dahl et al. . |
| 4,840,186 | 6/1989 | Lekholm et al. ........................ 607/116 |
| 5,330,520 | 7/1994 | Maddison et al. . |
| 5,483,022 | 1/1996 | Mar . |

*Primary Examiner*—William E. Kamm
*Assistant Examiner*—George R. Evanisko
*Attorney, Agent, or Firm*—Cushman Darby & Cushman IP Group of Pillsbury Madison & Sutro LLP

[57] ABSTRACT

A catheter for delivering electrical energy to a selectable region of a patient's body has at least one layer of fibers with at least one electrically conductive fiber stranded over a flexible core. Each layer of fibers is stranded over the flexible core and underlying layers opposite in direction from that of the immediately preceding layer so as to provide a catheter with good torque transfer properties in addition to its electrical energy transfer properties. The outermost layer of stranded fibers is electrically conductive and is covered by an electrically insulative outer layer which is mechanically strippable to expose selectable regions of the underlying layer of stranded fibers. Electrical energy is transmitted along the outermost layer of stranded fibers to tissue which is in contact with the exposed contact region of the outermost layer of stranded fibers. The catheter can also deliver electrical energy through a cutting tip for multipolar electro-cautery.

14 Claims, 6 Drawing Sheets

CATHETER FOR DELIVERY OF ELECTRIC ENERGY AND A PROCESS FOR MANUFACTURING SAME

This application is a continuation-in-part of application Ser. No. 08/662,799, filed Jun. 12, 1996.

BACKGROUND OF THE INVENTION

1. Field of the Invention

The present invention pertains to catheters for delivering electrical energy to internal regions of a patient's body, and more particularly to an electrical energy delivering catheter with stranded electrically conductive wires.

2. Description of Related Art

The term "medical catheter" is a reference to a very large class of known medical devices which share the general feature that they all tend to be tubular in shape and have a sufficiently small diameter such that they may be inserted into the patient's body through either a small incision or a small natural opening. A more specific, yet still somewhat broad, class of catheters has one or more electrodes such that electrical energy may be transferred between the external end of the catheter and internal regions of a patient's body. Such energy transfer can be for either therapeutic or diagnostic functions, or a combination of both. For example, such electrical catheters are known for mapping out the electrical activity of a patient's heart in order to provide data to assist a doctor in making a diagnosis. Electrical catheters are also used as therapeutic instruments to ablate tissue in specific regions of the body, such as heart tissue. Ablative catheters are known which employ a radio frequency electrical power source. Electrical catheters are also known for use in artificially pacing the heart and in defibrillation. The specific number of electrodes employed, the size of the electrodes, and the relative spacing and location of the electrodes on the electrical catheter depend on the particular application.

Many applications require a relatively large surface contact region which serves as the electrical energy transfer electrode. In addition, most applications that require large electrical contact regions also require adequate flexibility such that the catheter can be maneuvered to the desired location, such as a specific region of the heart, and yet be stable and controllable enough to be kept in place.

Prior art devices which simply utilize electrically conductive wires are unsatisfactory as electrodes. The configurations of electrical wires known in the art have smaller contact surfaces than are necessary, and, although such catheters are sufficiently flexible, they are extremely difficult to maintain in good contact with the specific tissue region.

Other prior art devices utilize a thin layer of conductive paint as an electrode. Such devices have the advantages of providing large contact areas and being mechanically flexible. However, they have the disadvantages that the conductive paint tends to chip, peel, and separate from the connecting wire due to the flexing action of the catheter. Therefore, many prior art devices utilize metal rings for the contact region in order to minimize the problems inherent in catheters which use conductive paint. However, catheters with ring electrodes also have problems and limitations. Most fundamentally, the rings are not flexible, thus only small rings are used. These devices also have the problem that one must maintain a good electrical connection between a wire, which typically moves with respect to the ring electrode as the catheter flexes, and the ring electrode. In addition, elaborate production methods are used in order to ensure that the metal ring does not protrude beyond the surrounding surface of the catheter.

Finally, still other prior art devices utilize electrically conductive wires which are braided in a cylindrical mesh which somewhat resembles the pattern of a fishing net. This type of prior art device has several disadvantages. The overlapping wires create spaces which prevent packing the wires closely together. The overlapping wires also create stresses and strains which can lead to breakage thus degrading the electrical and mechanical properties of the catheter. In addition, the overlapping wires create gaps which allow the overlying electrically insulative layer to adhere firmly to individual wires. This makes it difficult to mechanically strip away portions of the insulation without damaging the underlying wires.

Another type of catheter, a fiber optic catheter, is known to provide stranded optical fibers thus yielding increased flexure characteristics, an even distribution of bending stresses in the fibers, and a smaller overall diameter for the catheter. (See Wardle et al., U.S. Pat. No. 5,415,653).

It is known in the art that stranding optical fibers such that they define non-overlapping helical paths around a core provides desirable torque transfer properties for rotations of the optical catheter in one direction about its central axis. It is further known that by stranding a plurality of layers of optical fibers such that the direction of stranding is reversed for each successive layer added to the optical catheter provides an optical catheter with good torque transfer properties for rotations in both directions around the central axis of the catheter and good tactile qualities.

One application of stranded optical fibers is to form a laser sheath using optical fibers which conduct pulsed ultraviolet light to the tip of the device such that the light cuts tissue. Typically, excimer lasers are used as light sources. Excimer lasers have the disadvantage of being large, heavy, expensive, and consequently they are often not available. This has led to including two electrodes at the tip of a plastic sheath so as to cut tissue by bipolar electro-cautery. A typical application requires threading a pacing lead, which is attached to the patient's heart, through a central lumen of the electro-cautery catheter such that the pacing lead can be removed. A disadvantage of such a device is that it requires the sheath to be maneuvered over the lead such that it advances in a spiral motion so that it cuts scar tissue around the entire circumference of the lead as the sheath advances.

SUMMARY OF THE INVENTION

Accordingly, it is an object of this invention to provide a catheter for delivering electrical energy to an internal region of a patient's body through a stable, controllable, and flexible electrical contact region which can be made suitably large.

It is another object of this invention to provide a catheter for delivering electrical energy to an internal region of the patient's body which has no separate electrical connections to the electrical contact region, thus enhancing the reliability of the catheter.

It is another object of this invention to provide a catheter for delivering electrical energy to an internal region of the patient's body through one or more selectable electrical contact regions, such that the size, location, and relative separations of the contact regions are easily and cheaply selectable.

It is a further object of an embodiment of this invention to provide a catheter for electrical energy delivery to an internal region of the patient's body which has at least one electrical conduit of closely or maximally packed electrical wires which closely approximate an electrically conductive cylindrical shell.

It is another object of this invention to provide a catheter for electrical energy delivery to an internal region of the patient's body which has good torque transfer, good maneuverability, and good tactile characteristics.

It is yet another object of this invention to provide a catheter for electrical energy delivery to an internal region of the patient's body which incorporates a plurality of sensors while having good reliability and a good profile.

Still another object of the present invention is to provide a catheter for delivering electrical energy to an internal region of a patient's body through a tip for cutting tissue so that the electrical energy for cutting tissue is distributed approximately symmetrically around the circumference of the cutting tip.

Another object of the present invention is to provide a flexible and easily maneuverable catheter for delivering electrical energy to an internal region of a patient's body through a tip for cutting tissue.

It is also an object of the present invention to provide a method of manufacturing each embodiment of electrical energy delivering catheters as described in the above objects of this invention.

The above and related objects of the instant invention are realized by stranding electrically conductive fibers over a flexible core. A layer of stranded fibers is comprised of a plurality of fibers which extend substantially between both ends of the catheter along non-overlapping paths, preferably in spiral or helical paths. Since the fibers do not overlap, they can be closely or maximally packed together in a layer which approximates a cylindrical shell conductor. Such a layer of stranded fibers provides a conducting conduit between both ends of the catheter and provides an outer surface to make electrical contact. Thus, the limit for the largest surface contact region for a given catheter, according to an embodiment of this invention, is equal to the entire outer surface of the electrically conductive surface layer. Generally, one will utilize only a fraction of the surface of the stranded layer as an electrical contact region. Therefore, the catheter is typically covered with an outer electrically insulative layer which is mechanically stripped to expose the desired electrical contact regions. The invention has an advantage that the insulative layer is easy to mechanically strip without damaging the underlying layer of stranded fibers.

This yields a flexible catheter for electrical energy delivery which has suitably large electrical contact regions and a low resistance electrical conduit which flows directly into the contact regions without the need for any electrical connections therebetween.

Preferably, the wires are stranded in non-overlapping helical paths around the core with a substantially uniform pitch. In other embodiments of the instant invention, additional stranded and insulative layers are provided between the insulating core and the outer stranded layer to provide certain desirable mechanical and/or electrical properties.

A preferred embodiment of the instant invention also comprises a first layer of stranded fibers over the central core, and a second layer of stranded fibers over the first layer of stranded fibers. The plurality of fibers in each layer of stranded fibers define non-overlapping helical paths with a substantially uniform pitch. Each successive layer of stranded fibers is wound around the underlying structure in a direction opposite to that of the preceding layer of stranded fibers.

In another embodiment of the invention, at least one layer of stranded fibers is made of metal wires which are connected to ground such that they provide a shield for electric fields. Other embodiments of the invention combine alternative combinations of stranded and insulating layers to achieve certain mechanical and electrical structures.

In a preferred embodiment of the invention, the core defines a central lumen which is suitable for accommodating at least one wire or fiber. In other embodiments of the invention, the core defines a plurality of lumens.

In other embodiments of the invention, different types of fibers are mixed with electrically conductive fibers. Optical fibers are included in an embodiment of the invention to carry optical sensor signals or therapeutic energy. In another embodiment of this invention, certain polymer fibers are included to provide enhanced lubricity of the corresponding stranded layer.

In another embodiment of the invention, at least one layer of stranded fibers includes a plurality of electrically conductive fibers. The electrically conductive fibers are preferably exposed at one end of the catheter so as to provide a tip for cutting tissue by electro-cautery. The energy to perform the electro-cautery is applied in bipolar or multipolar modes between metal fibers in the device by a surgical electro-cautery power unit.

The instant invention also encompasses a process for manufacturing an electrical energy delivering catheter by stranding at least one plurality of fibers over a flexible non-conductive core.

DETAILED DESCRIPTION OF THE PREFERRED EMBODIMENTS

Figure 1:
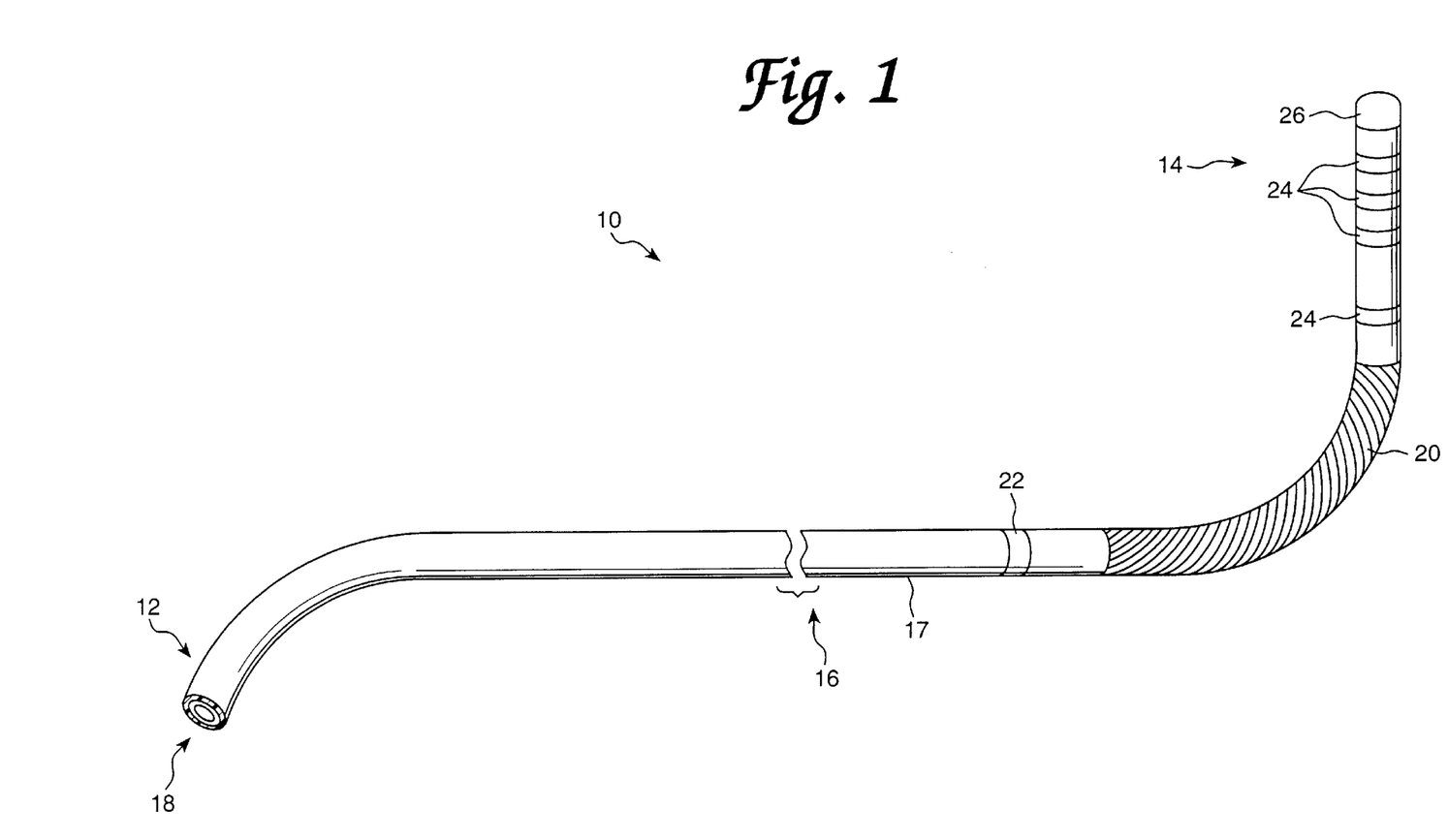
FIG. 1 is a schematic view of a catheter for delivering electrical energy to a region of a patient's body according to the preferred embodiments of the invention.

The catheter of the present invention is designated generally by the reference numeral 10 in FIG. 1. The catheter 10 is depicted with the central section broken away. Consequently, FIG. 1 gives no indication of the length of the catheter 10 relative to its width. The length of the catheter 10 is selectable in accordance with the length of known catheters which are used for the same or similar applications. Generally, the catheter 10 defines a proximal end 12, a distal end 14, and an outer surface 16, with the outer surface being approximately cylindrical in shape within local regions along the length of the catheter 10.

In a preferred embodiment, the outer surface 16 of the catheter 10 is defined by an outer electrically insulating surface layer 17 which fits snugly over an inner composite structure 18. For most uses of this invention, polyurethane is a preferable material for the outer insulating layer 17. However, there are a large number of suitable materials that would be well known to those skilled in the art. For example, polyester ether ketone is a preferable material for the insulating layer 17 in ablative catheters. The outer surface layer 17, in this embodiment, is mechanically strippable at a selectable contact region 20 so as to expose the outer layer of the inner composite structure 18 over the selectable contact region 20. In the example illustrated in FIG. 1, sensors 22 and 24 are attached to selectable locations along the catheter 10, and sensor 26 is attached to the distal end 14.

Figure 2:
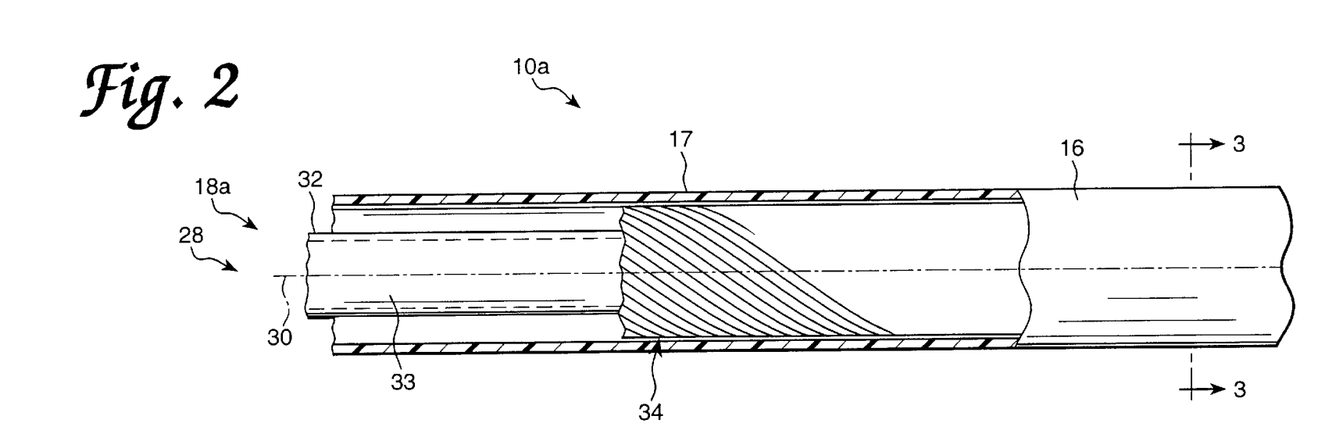
FIG. 2 is a partial cutaway view which shows the inner composite structure of a first embodiment of the invention.
Figure 3:
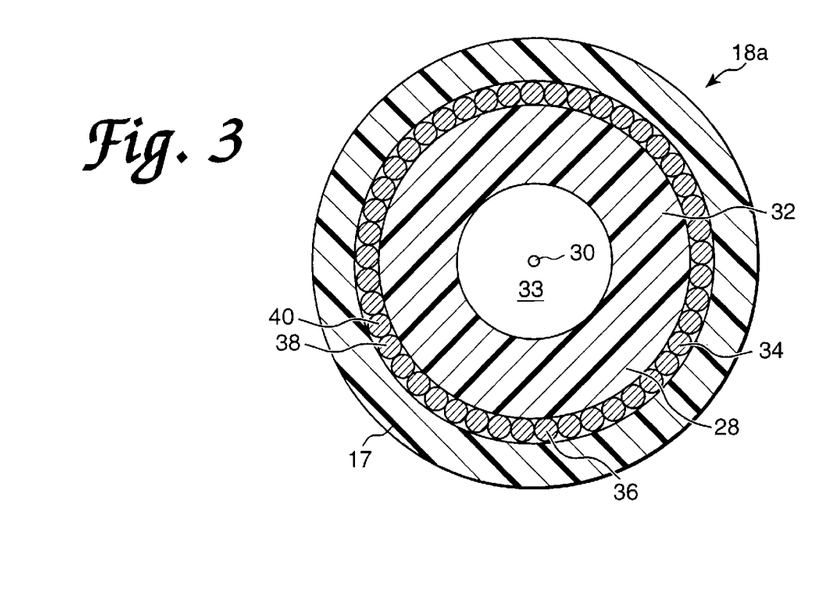
FIG. 3 is a cross-sectional view of the first embodiment taken on section line 3—3 in FIG. 2.

One can best see the inner composite structure 18a of a preferred embodiment in FIGS. 2 and 3. FIG. 2 is a side view of a section of the catheter 10a with partial cutaway sections which reveal the inner composite structure 18a. FIG. 3 provides a cross-sectional view of the catheter 10a. The catheter 10a is generally comprised of a central flexible, electrically non-conductive core 28 disposed along the catheter axis 30. (The term "non-conductive" is used to refer to any material which is generally known to be an insulator, or to a fluid or gas-filled or vacuum space which also acts as an insulator.) In one embodiment of the invention, the core 28 is a solid electrical insulator, and in other embodiments the electrically insulative core 28 defines one or more hollow paths that extend between the proximal end 12 and the distal end 14 of the catheter 10a. In a preferred embodiment, the central non-conductive core 28 is flexible electrically insulative tubing 32 which defines a central lumen 33 that extends along the catheter axis 30. In the preferred embodiment the core is made of polyurethane.

The non-conductive core 28 has a layer of stranded fibers 34 on its outer surface. Stranding optical fibers in a fiberoptic catheter is taught by Wardle et al. in U.S. Pat. No. 5,415,653 entitled "Optical Catheter with Stranded Fibers," and is hereby incorporated by reference in its entirety. The first layer of stranded fibers 34 is comprised of a plurality of fibers, one of which is designated by reference numeral 36 in FIG. 3. Each fiber, such as fiber 36, in the layer of stranded fibers 34 extends substantially between the proximal end 12 and the distal end 14 of the catheter 10a, along non-overlapping, helical paths around the central non-conductive core 28.

The stranded fibers 34 define helical paths with a substantially uniform first pitch angle for all fibers 34 at substantially all points along the helical paths when the catheter 10a subtends a straight line and is in an unstressed, relaxed state.

Generally, each individual fiber, such as fiber 36, has a selectable thickness and composition. For example, fiber 38 may have a different thickness from that of fiber 36, or fiber 38 may be of a different material from that of fiber 36. The layer of stranded fibers 34 is nowhere thicker than the thickness of the thickest fiber. In the example depicted in FIGS. 2 and 3, the fibers 34 are 40±4 electrically conducting wires which are all of approximately equal thickness. The example depicted in FIG. 3 shows individual adjacent fibers, such as fibers 38 and 40, as being contiguous. Other embodiments of this invention include selectable numbers of fibers within the layer of stranded fibers 34, and selectable separations between fibers. The number of fibers are chosen to be greater than 10, preferably 20 or more, and are often chosen in the range of 40, 50, or even greater. In many uses, such as to deliver high voltage defibrillation pulses, the fibers are preferably made from low resistance materials such as platinum, silver or titanium. In this embodiment, the stranded fibers 34 are covered by insulating layer 17 described above.

Figure 4:
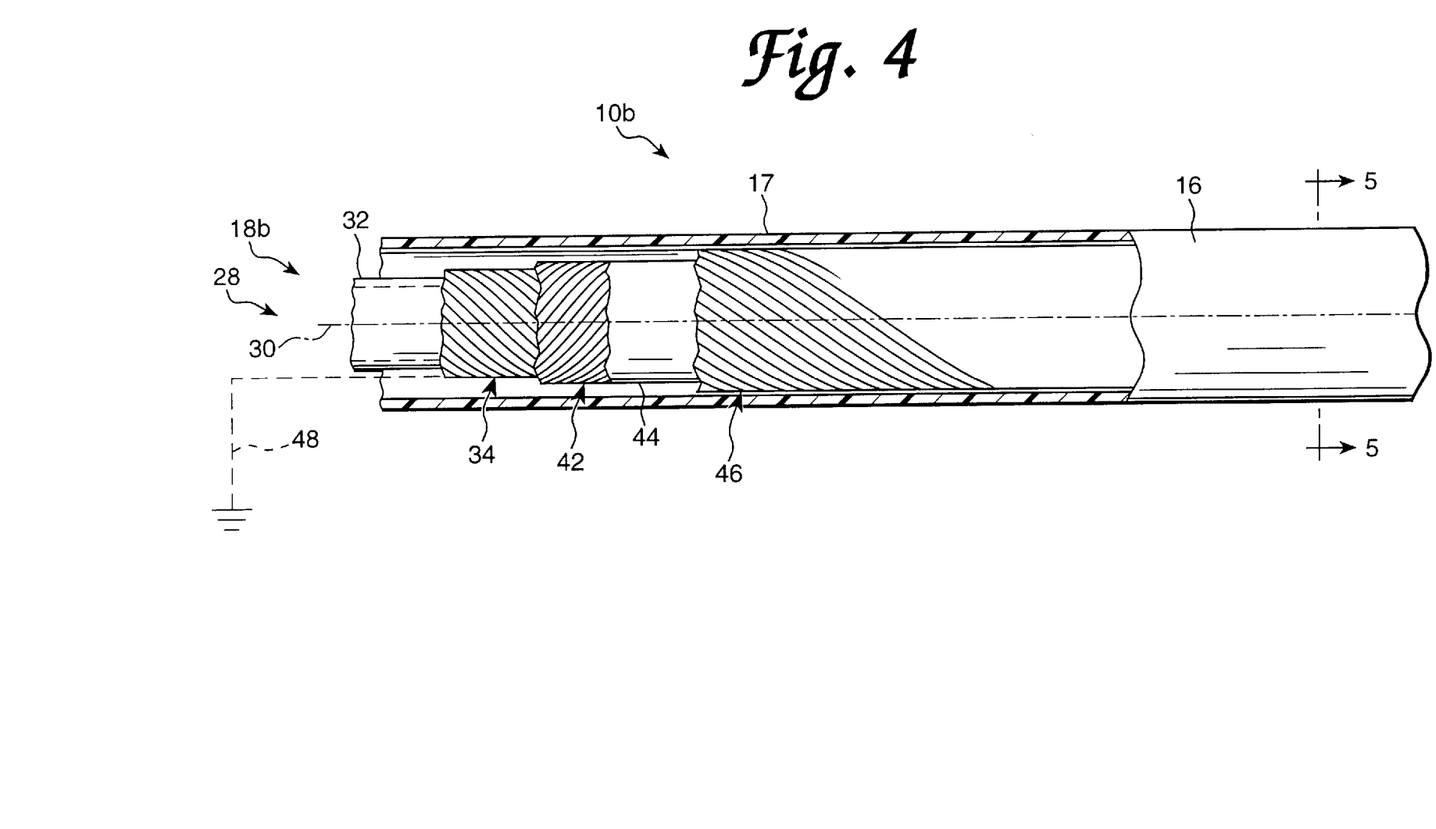
FIG. 4 is a partial cutaway view which shows the inner composite structure of a second embodiment of the invention.
Figure 5:
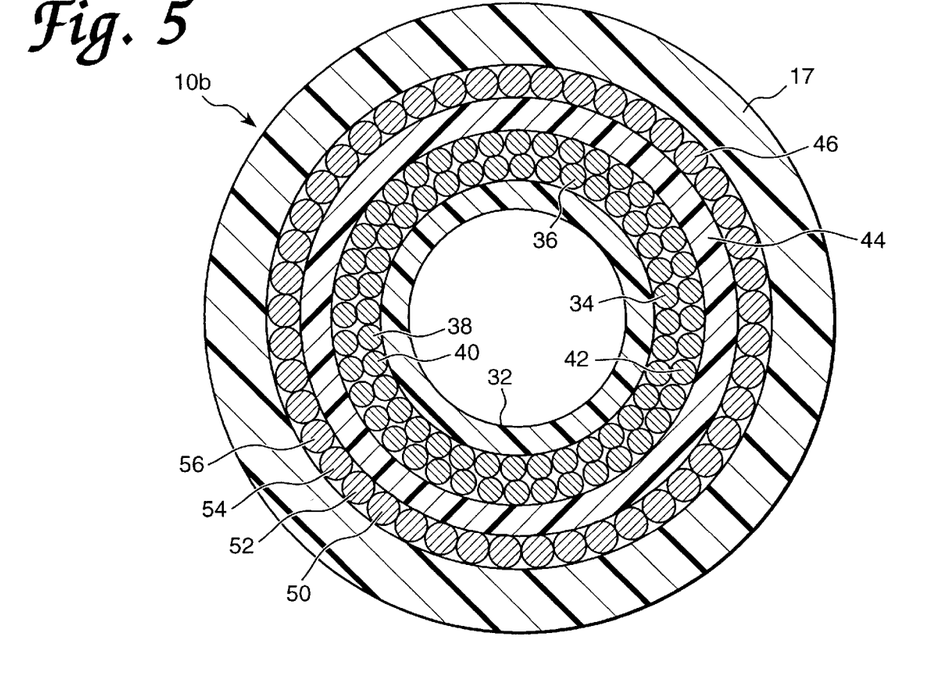
FIG. 5 is a cross-sectional view of the second embodiment of the invention taken on section line 5—5 in FIG. 4.

One can best see the inner composite structure 18b of another preferred embodiment in FIGS. 4 and 5. FIG. 4 is a side view of a section of the catheter 10b with partial cutaway sections which reveal the inner composite structure 18b. FIG. 5 provides a cross-sectional view of the catheter 10b. The catheter 10b is generally comprised of a central flexible, electrically non-conductive core 28 disposed along the catheter axis 30, as described above in reference to the first mentioned preferred embodiment.

This embodiment has a first layer of stranded fibers 34 on the outer surface of the non-conductive core with a second layer of stranded fibers 42 immediately over the first layer of stranded fibers. In this preferred embodiment of the invention, each successive layer of fibers is stranded over the underlying layer in a direction opposite to that of the closest underlying stranded layer. Therefore, according to this preferred embodiment of the invention, the second layer of stranded fibers 42 is stranded over the first layer of stranded fibers 34 in a direction opposite to that of the first layer. The individual fibers of the second layer of stranded fibers 42, and any and all succeeding layers of stranded fibers, are selectable in material and thickness. In a preferred embodiment of the instant invention, there are 38±4 fibers in the first layer and 43±4 fibers in the second layer which are all substantially of equal thickness. The fibers of the first and second layers in this embodiment are preferably of materials with high tensile strength, such as stainless steel. The fibers of the second layer of stranded fibers 42 similarly extend between the proximal end 12 and the distal end 14 of the catheter 10b along non-overlapping helical paths around the first layer of stranded fibers 34. The second layer of stranded fibers 42 is also stranded such that the plurality of fibers define helical paths of a substantially uniform second pitch for all fibers 42 at substantially all points along the helical paths when the catheter 10b subtends a straight line and is in an unstressed, relaxed state. Since the second layer of stranded fibers 42 is stranded around the first layer of stranded fibers 34 in a direction opposite from that of the direction in which the first layer of stranded fibers 34 is stranded around the non-conductive core 28, the second pitch is opposite in sign to that of the first pitch.

Furthermore, the magnitude of the second pitch is approximately equal to the magnitude of the first pitch, which is preferably 0.475 inches. The reader should note that it is known in the art that the pitch of layers of stranded optical fibers can be selectively varied to achieve alternative mechanical properties of a fiberoptic catheter. A greater pitch allows one to strand a greater number of fibers at the expense of some flexibility and torquability. Conversely, a smaller pitch leads to greater flexibility, but a smaller number of fibers in the strand. Similarly, in other embodiments of the instant invention, one can select different and nonuniform first and second pitches in order to obtain desired mechanical properties. Preferably, the pitch is much greater than the thickness of the wire (at least 10 times greater, and more typically more than 40 times greater).

The preferred embodiment depicted by the example of FIGS. 4 and 5 has a first electrically insulative layer 44 immediately covering the second layer of stranded fibers.

Polyurethane is a suitable material for layer 44 for most uses, or polyester ether ketone for other uses. A third layer of fibers 46 is stranded over the outer surface defined by the first electrically insulative layer 44. In a preferred embodiment, the third layer of stranded fibers 46 has 40±4 titanium wires, each of which extend substantially between the proximal end 12 and the distal end 14 of the catheter 10b, along non-overlapping helical paths with a third pitch which is substantially equal in magnitude, but opposite in sign to the second pitch. The third layer of stranded fibers 46 is covered by a second layer of electrically insulative material 17 which defines an outer surface 16. When the present embodiment is used as a defibrillation catheter, the second layer of electrically insulative material 17 must be capable of withstanding a DC voltage of 1500V applied in 20 ms pulses. A layer 17 made of polyurethane with a thickness of at least 0.0035 inches is suitable for catheter 10b with an outer diameter of 0.077±0.002 inches.

In the preferred embodiments of this invention the outermost layer of stranded fibers has a large number of closely or maximally packed electrically conductive fibers. The fibers are arranged so as to approximate an electrically conductive cylindrical shell. The approximation to a cylindrical shell improves as the number of fibers increases. Conversely, small numbers of fibers cannot provide a good approximation to a cylindrical shell, as one can appreciate by considering the extreme cases of only one, two, three or four fibers.

The central lumen of the non-conductive core 28 is adapted to accommodate a plurality of fibers which, in one embodiment, extend between the proximal end 12 and the sensors 22, 24, and 26. More particularly, in a preferred embodiment, the central lumen of the non-conductive core 28 accommodates electrically conductive wires which extend from the proximal end 12 of the catheter 10b to connect to electrodes on the sensor 22, 24, and 26.

The electrodes on sensor 26 are suitable for mapping the electrical activity of the heart by procedures which are well-known to one skilled in the art of modern electrophysiology.

In practice, the catheter 10 is guided through a small incision in the body to the internal regions of interest. The flexible inner core 28, first layer of stranded fibers 34, second layer of stranded fibers 42, first insulating layer 44, third layer of stranded fibers 46, and outer surface layer 17 all act in cooperation to transmit torque between the proximal end 12 and the distal end 14 in a manner known in the art for stranded optical fibers. Depending on the particular application, the electrically conductive fibers of the third (outermost) layer of stranded fibers 46 are electrically connected to a high voltage source, a radio frequency voltage source, signal detection and processing equipment, or other suitable electronic equipment. The contact region 20 provides a suitably large surface area for making electrical contact with the internal region of the body of interest. The contact region 20 is selectable in both size and location along the catheter 10 by stripping away the corresponding material from the electrically insulating surface layer 17. In addition, other embodiments of the instant invention have a plurality of contact regions, similar to contact region 20, which are also selectable in size and location. It is important to point out that, unlike prior art ring electrodes, the contact region 20 does not severely affect the flexibility of the catheter and does not present protruding obstacles. As a specific example, one may connect a high voltage source to the third layer of stranded fibers 46 to deliver defibrillation pulses to a patient's heart through the contact region 20. The outer insulating layer 17 and the first electrically insulative layer 44 ensure that the third layer of stranded fibers 46 is electrically isolated everywhere except at the proximal end 12 of the catheter 10, and at the contact region 20.

In a preferred embodiment of the instant invention, the first layer of stranded fibers 34 and the second layer of stranded fibers 42 are electrically isolated from the central lumen by the electrically insulating core 28, and from the third layer of stranded fibers 46 by the first insulative layer 44. In this embodiment, the first layer of stranded fibers 34 and the second layer of stranded fibers 42 have no electrical connections and thus provide primarily mechanical torque transfer properties. In another preferred embodiment, the first layer of stranded fibers 34 and the second layer of stranded fibers 42 are electrically connected to ground as indicated schematically in FIG. 4 by the reference numeral 48. It can also be readily understood by one of ordinary skill in the art, based upon the teachings of this invention, that the layers 34 and 42 provide a second layer in which electrical energy can be transferred between the proximal end 12 and distal end 14 of the catheter 10, independently of the third layer of stranded fibers 46. Energy transfer along this second channel can be in the form of signals from sensors, for example, or for therapeutic purposes.

In other embodiments of the instant invention, fibers of different materials can be mixed with the electrically conductive fibers. For example, fiber 50 in the third layer of stranded fibers 46, or fiber 40 of the first layer of stranded fibers could be an optical fiber suited for transferring optical signals between the distal end 14 and the proximal end 12 of the catheter 10. A greater number of such optical fibers could be used as necessary. The optical fibers could also be used to deliver therapeutic energy to a tissue site somewhere along the length, or at the distal end 14, of the catheter 10, in addition to the above described electrical energy transfer properties of the catheter 10.

In another embodiment of the instant invention, electrically insulative fibers can be mixed with the electrically conductive fibers. For example, as one may best see in FIG. 5, the fiber labeled with the reference numeral 50 may be an electrically conductive wire. The fiber 52 may be an insulative fiber, fiber 54 conductive, fiber 56 insulative, and so on around the third layer of fibers 46. This embodiment yields a plurality of separate electrically conductive channels, e.g., fiber 50 would be one channel, fiber 54 another channel, and so on. This embodiment of the instant invention is not limited to the one specific example described above. One could choose the numbers of electrically insulative and conductive fibers, and the specific configuration of those fibers, from among all of the possible permutations to suit the particular application.

In another embodiment of the instant invention, one may utilize a plurality of different fiber types in order to select specific mechanical properties, in addition to the electrical properties of the catheter 10, to suit a particular application. For example, a fiber such as fiber 40 in the first layer of stranded fibers 34, and any number of other fibers in any of the stranded layers, can be made from certain polymers so as to enhance the lubricity of the corresponding layer.

The preferred embodiment described in detail above, in which a first layer of fibers 34 is stranded over a central core 28, followed by a second layer of stranded fibers 42, a first layer of insulation 44, a third layer of stranded fibers 46, and finally an outer layer of insulation 17, does not limit the invention to that specific configuration. Other embodiments have various numbers of layers of stranded fibers configured with various numbers of intervening electrically insulative layers. Alternatively, the stranded fibers can be provided with an insulating or lubricious coating.

As noted, there are numerous advantages of the catheter of this invention over other catheters for the delivery of electrical energy. The catheter of this invention provides a relatively large surface contact region for transferring electrical energy to an internal region of the body and it is also flexible at the contact region. There are no electrical connections between the contact regions and the wires that transfer the electrical energy to the contact regions, such as is the case with the prior art ring electrodes, thus, enhancing the reliability of the catheter. There are no complicated manufacturing techniques required to ensure that the contact region does not protrude beyond the diameter of the adjacent regions of the catheter, so as not to obstruct the motion of the catheter through narrow paths within the patient's body. The electrically conductive fibers can be closely packed together, so as to approximate a cylindrical sheet conductor.

A plurality of wires which carry an electrical current to the surface contact region has a lower overall resistance than a single wire of the same material of the same thickness that carries the same amount of current to contact regions. Therefore, the stranded wires allow the current to be spread over a region which approximates a cylindrical shell of current. As one strands wires closer together, one more closely approximates the limit of an electrically conductive cylindrical shell. This is particularly true when the wires are stranded so closely together that they are in contact with the immediately adjacent fibers. In such a case, if the wires do not have insulating outer layers, current can then also flow between wires. This additional degree of freedom for the flow of electrical current leads to an additional decrease in the overall electrical resistance, thus, even more closely approximating a conducting ring while remaining flexible.

Therefore, this invention minimizes undesirable resistive heating effects while still providing a central lumen for other instruments and sensors, all while maintaining a compact, narrow cross-section.

Figure 6:
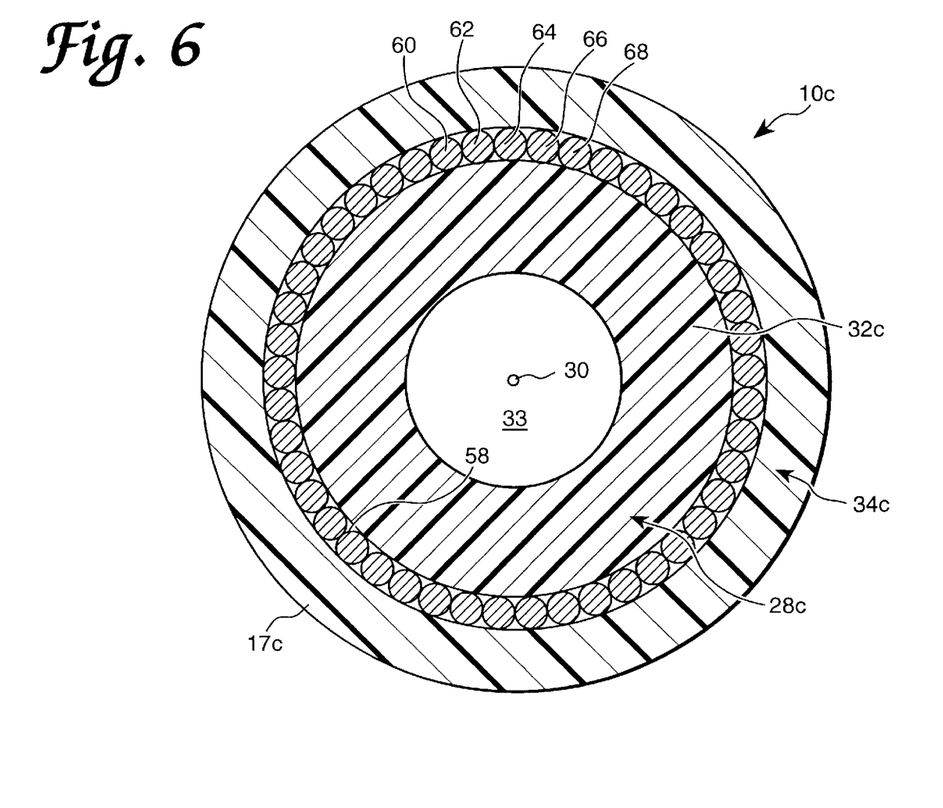
FIG. 6 is an end-on view of the distal end of the catheter of the invention according to a third preferred embodiment of the invention.

In a third preferred embodiment of the instant invention, the catheter 10c has an outer insulating layer 17c, at least one layer of stranded fibers 34c comprising a plurality of electrically conductive wires, and a non-conductive core 28c which is preferably electrically insulative tubing 32c that defines a central lumen 33 (see FIG. 6). The plurality of electrically conductive wires can have various configurations. Preferably, the fibers are stranded in nonoverlapping helical paths in a manner as described in the first and second embodiments of this invention.

Figure 8:
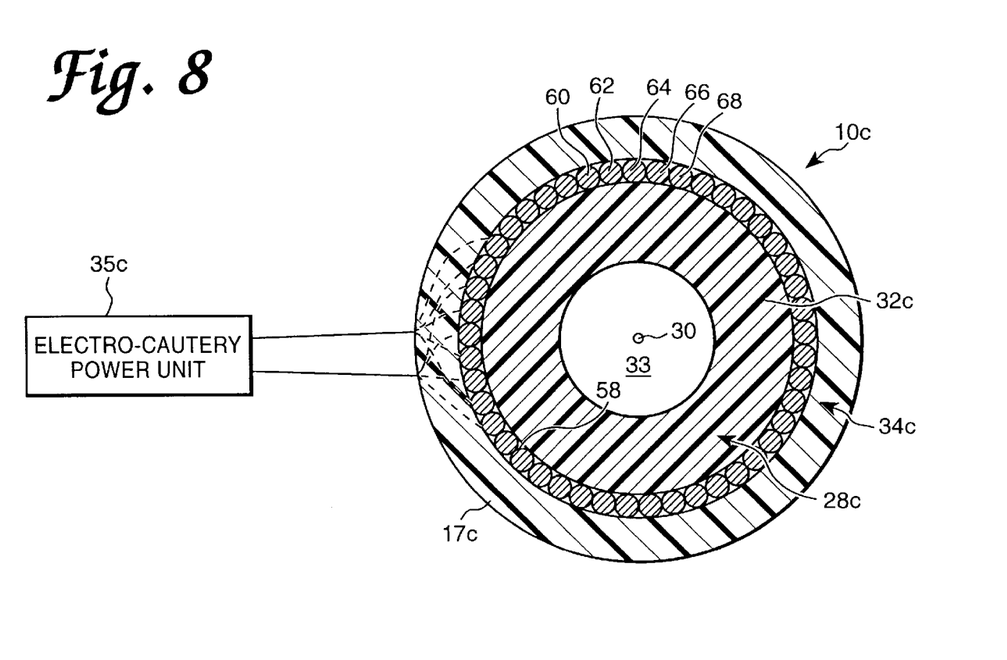
FIG. 8 is a schematic illustration of a first embodiment of an electro-cautery device according to this invention.

In this embodiment, all of the fibers of the layer of stranded fibers 34c are preferably electrically conductive wires that have electrically insulating outer layers, such as outer layer 58. The electrically conductive wires of the layer of stranded fibers 34c are preferably connected at the proximal end to a surgical electro-cautery power unit 35c (see, FIG. 8) such that each fiber has a polarity opposite to that of the two adjacent wires. The surgical electro-cautery power unit may be selected from conventionally known power units to provide electrical pulses for cutting tissue. For example, wire 62 has a polarity opposite to that of wires 60 and 64. Similarly, wire 64 has a polarity opposite to that of wires 62 and 66, and so on around the entire periphery of the layer 34c of electrically conductive wires.

One skilled in the art would recognize that other arrangements of the wires of the layer 34c are possible without departing from the scope or spirit of the invention. For example, electrically non-conductive fibers may be included within the layer of stranded fibers 34c. Such non-conductive fibers may be disposed between electrically conductive wires within the layer of stranded fibers 34c in numerous configurations. In such alternative embodiments, the electrically non-conductive fibers may be disposed between electrically conductive wires to form configurations in which the electrically conductive wires are distributed about the catheter axis 30 in symmetrical and in asymmetrical patterns.

In another alternative embodiment, the electrically conductive fibers within the layer of stranded fibers 34c do not have electrically insulating surfaces. Instead, electrically insulating fibers, along with electrically insulating layers 17c and 32c, keep electrically conductive wires of one polarity electrically isolated from wires of the opposite polarity along the length of the catheter 10c. For example, fibers 60, 64, and 68 in FIG. 6 are electrically non-conductive, fiber 62 is an electrically conductive wire attached to the power source 35c at one polarity, and fiber 66 is an electrically conductive wire with the polarity opposite to that of wire 62. This pattern is repeated around the entire layer of stranded fibers 34c.

FIG. 6 is an end-on view of the catheter 10c which illustrates the exposed ends of the wires 60, 62, 64, etc. which form the cutting end according to the third preferred embodiment.

In practice, the cutting end of the layer of stranded fibers 34c is brought into contact with tissue to be cut. Electrical energy is transmitted through wires 60, 62, 64, etc. from the electro-cautery power unit at the proximal end of the catheter 10c to the cutting end at the distal end of the catheter 10c. An electrical current thus flows through tissue in contact with the tip and between wires of opposite polarities, e.g., wires 60 and 62. The relatively high resistance, or impedance, of the tissue results in a rapid dissipation of energy in the tissue that is in contact with the tip. The rapid dissipation of energy in the tissue acts to a cut the tissue. Since all the fibers of the layer of stranded fibers 34c are electrically conductive wires, with electrically insulating surfaces, the cutting effect is approximately uniformly distributed around the cutting tip end of the layer of stranded fibers 34c.

In one method of application, the catheter 10c is used for removing pacing leads for heart pacemakers which had previously been implanted in the patient's body. In such an application, the surgeon slides the catheter 10c over the pacing lead such that the pacing lead extends along the central lumen 33. Since the cutting effect is approximately uniformly distributed around the cutting tip, the surgeon can advance the catheter 10c along the pacing lead in a substantially rectilinear motion without the need to rotate the catheter by large amounts about the catheter axis 30. However, one can anticipate that some small angle "back and forth" rotations about the catheter axis 30 as the catheter 10c is advanced over the pacing lead can be advantageous in some cases. Therefore, this permits the surgeon to advance the catheter along the pacing lead while cutting scar tissue around the entire circumference of the lead, thus obviating the need to advance the catheter in a spiral motion over the pacing lead. Although this embodiment of the invention was described for removing pacing leads, this embodiment of the invention is also useful for other types of surgery, such as removing tumors, biopsies, and other implant devices.

Figure 7:
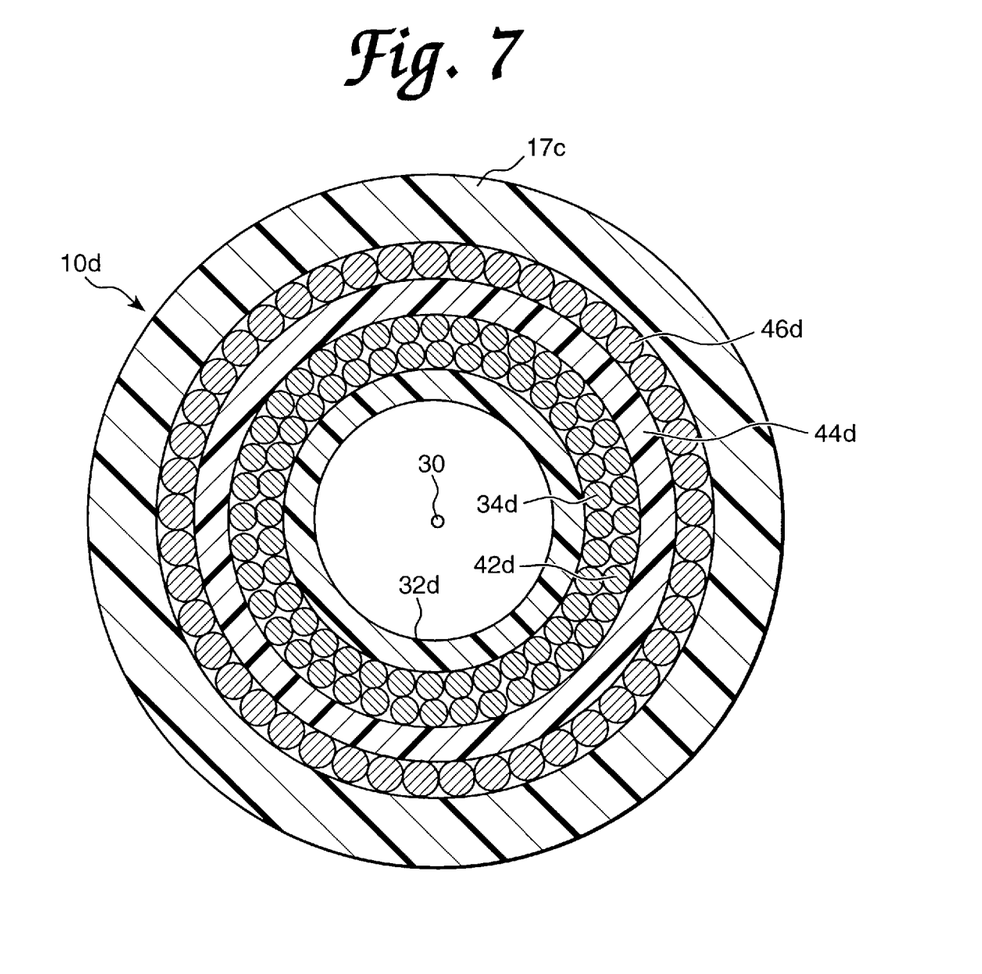
FIG. 7 is an end-on view of the distal end of the catheter of the invention according to a fourth preferred embodiment of the invention.

In the fourth embodiment of the invention, illustrated in FIG. 7, the catheter 10d has a plurality of layers of stranded fibers. FIG. 7 is an end-on view of the cutting tip at the distal end. In one example of this embodiment, the layer of stranded fibers 46d corresponds to the layer of stranded fibers 34c of the third embodiment, thus providing the cutting action. The layers of stranded fibers 34d and 42d correspond to the layers of stranded fibers 34 and 42 of the second embodiment. Consequently, the additional layers of stranded fibers 34d and 42d provide the mechanical advantages of good maneuverability for a catheter for electro-cautery.

Figure 9:
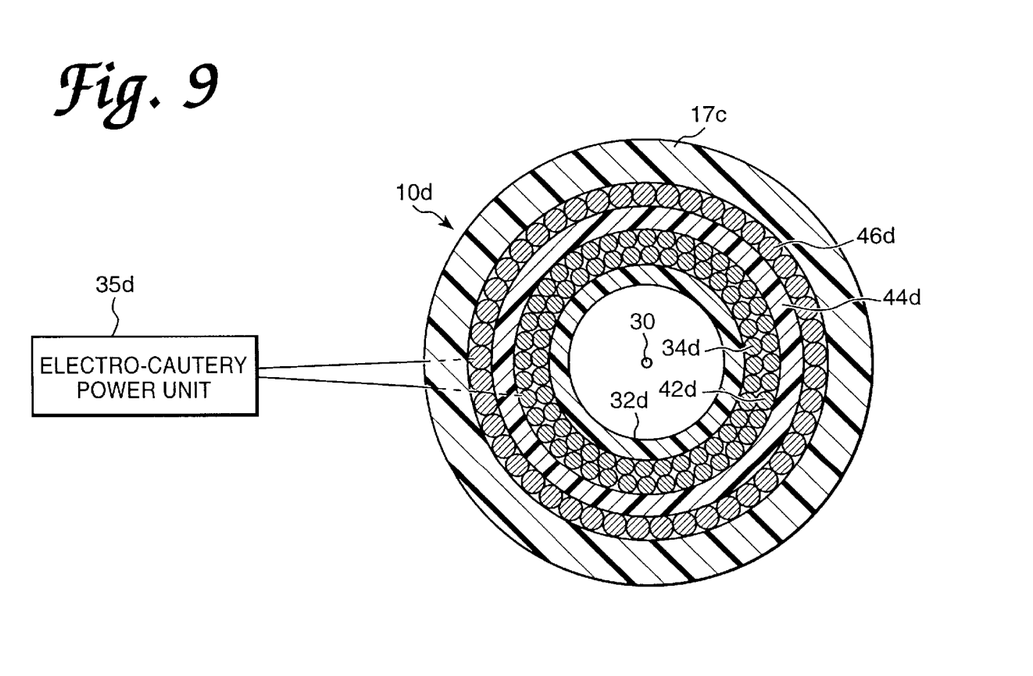
FIG. 9 is a schematic illustration of a second embodiment of an electro-cautery device according to this invention.

In another example of the fourth preferred embodiment of the invention, substantially all fibers in the layer of stranded fibers 46d are electrically conductive wires which are in Electrical contact with each other. Similarly, the layers of stranded fibers 34d and 42d are substantially all electrically conductive wires which are in electrical contact with the adjacent fibers. Preferably, the layer 46d is connected at the proximal end to a surgical electro-cautery power unit 35d (see, FIG. 9) at one polarity while the layers 34d and 42d are connected at the opposite polarity. The layer 44d is an electrically non-conductive layer which keeps layer 46d electrically isolated from layers 34d and 44d along the length of the catheter. Preferably, the layers are stranded in nonoverlapping helical paths in the same manner as in the second embodiment.

In operation, the distal end of the catheter is brought into contact with tissue. The tissue provides a conductive, but high resistance, or high impedance, path for electricity to flow between layer 46d and layers 34d and 42d at the distal end. The high resistance, or impedance, of the tissue in contact with the catheter 10d at its distal end results in a rapid absorption of energy by the tissue which acts to provide the cutting effect.

Catheters according to the fourth embodiment of the invention may be used according to the same method of pacing lead removal as described with respect to the third embodiment. In addition, this embodiment of the invention is also useful for other types of surgery, such as removing tumors, biopsies, and other implant devices.

One skilled in the art would recognize that alternative arrangements of pluralities of layers of stranded fibers and electrically non-conductive layers are within the scope and spirit of the instant invention. For example, there may be only two layers 42d and 46d, separated by an electrically non-conductive layer 44d. There may also be more than three layers of stranded fibers with more than one electrically non-conductive layer disposed between layers of stranded fibers.

Although the invention has been described with reference to specific embodiments, one should realize that these embodiments are illustrative of the application of the principles of the invention. One should recognize from the above description that there are a very large number of modifications and rearrangements of the above-illustrated embodiments which one may devise without departing from the spirit and scope of the invention.

What is claimed is:

1. A catheter comprising:
    a core having an axis extending between a proximal end and a distal end of said catheter;
    a layer of stranded fibers having a plurality of fibers that extend between said proximal end and said distal end of said catheter over said core; and
    an electrically non-conductive layer disposed over said layer of stranded fibers so as to prevent a flow of electrical current in a radial direction through said electrically non-conductive layer,
    wherein said layer of stranded fibers comprises a plurality of electrically conductive wires that extend to a most distal end of said catheter to form an electro-cautery cutting tip at said distal end of said catheter, and
    said plurality of electrically conductive wires that form said electro-cautery cutting tip are brought directly into contact with tissue to be cauterized.

2. A catheter according to claim 1, wherein substantially all fibers of said layer of stranded fibers are electrically conductive wires with electrically insulating outer layers so as to electrically isolate each wire along a length of the catheter from the proximal end to said distal end.

3. A catheter according to claim 2, wherein said core is flexible tubing that defines a hollow path extending between said proximal end and said distal end of said catheter such that said hollow path can accommodate at least a pacing lead threaded therethrough, and
    said layer of stranded fibers forms a substantially contiguous layer of stranded fibers enclosing said core therein, said substantially contiguous layer of stranded fibers having a maximum thickness in a radial direction substantially equal to a thickness of a thickest fiber of said plurality of fibers.

4. A catheter according to claim 3, wherein said fibers of said layer of stranded fibers extend from said proximal end to said distal end of said catheter along non-overlapping helical paths.

5. A catheter according to claim 1, further comprising:
    a second layer of stranded fibers having a plurality of fibers that extend between said proximal end and said distal end of said catheter over said core, said second layer of stranded fibers is disposed between said first mentioned layer of stranded fibers and said core; and
    a second electrically non-conductive layer disposed between said first mentioned layer of stranded fibers and said second layer of stranded fibers thereby preventing flow of electrical current between said first mentioned and said second layers of stranded fibers.

6. A catheter according to claim 5, wherein said second layer of stranded fibers comprises a second plurality of electrically conductive wires that extend to said most distal end of said catheter, said first mentioned and said second pluralities of electrically conductive wires form said electro-cautery cutting tip at said distal end of said catheter, said first mentioned and said second pluralities of electrically conductive wires that form said electro-cautery cutting tip being brought directly into contact with tissue to be cauterized.

7. A catheter according to claim 6, wherein substantially all fibers of said first mentioned layer of stranded fibers and said second layer of stranded fibers are electrically conductive wires.

8. A catheter according to claim 7, wherein said core is flexible tubing that defines a hollow path extending between said proximal end and said distal end such that said hollow path can accommodate at least a pacing lead threaded therethrough, and
    said layer of stranded fibers forms a substantially contiguous layer of stranded fibers enclosing said core therein, said substantially contiguous layer of stranded fibers having a maximum thickness in a radial direction substantially equal to a thickness of a thickest fiber of said plurality of fibers.

9. A catheter comprising:
    a core having an axis extending between a proximal end and a distal end of said catheter;
    a first layer of stranded fibers having a first plurality of fibers that extend between said proximal end and said distal end of said catheter over said core;

a second layer of stranded fibers having a second plurality of fibers that extend between said proximal end and said distal end of said catheter over said core, said second layer of stranded fibers being disposed between said first layer of stranded fibers and said core;

a first electrically non-conductive layer disposed over said first layer of stranded fibers thereby preventing a flow of electrical current in a radial direction through said first electrically non-conductive layer; and a second electrically non-conductive layer disposed between said first layer of stranded fibers and said second layer of stranded fibers thereby preventing a flow of electrical current between said first and said second layers of stranded fibers, wherein said first and said second layers of stranded fibers form an electro-cautery cutting end at said distal end of said catheter, substantially all fibers of said first layer of stranded fibers and said second layer of stranded fibers are electrically conductive wires, said core defines a hollow path extending between said proximal end and said distal end such that said hollow path can accommodate at least a pacing lead threaded therethrough, said first plurality of fibers extend from said proximal end to said distal end of said catheter along non-overlapping helical paths defining a first rotation direction, and said second plurality of fibers extend from said proximal end to said distal end of said catheter along non-overlapping helical paths defining a second rotation direction that is approximately equal in magnitude and opposite in sign to said first rotation direction.

10. A catheter according to claim 9, further comprising:

a third layer of stranded fibers having a plurality of fibers that extend between said proximal end and said distal end of said catheter over said core, wherein said third layer of stranded fibers is disposed between said second layer of stranded fibers and said core, and said fibers of said third layer of stranded fibers extend from said proximal end to said distal end of said catheter along non-overlapping helical paths defining a third rotation direction that is approximately equal in magnitude and opposite in sign to said second rotation direction so as to act in cooperation with said first mentioned and said second layers of stranded fibers to transmit torque along said axis of said catheter under rotations in both directions about said axis.

11. An electro-cautery device, comprising:

a catheter having an electro-cautery cutting end at a distal end of said catheter; and an electro-cautery power unit attached to a proximal end of said catheter, wherein said catheter comprises:

a core having an axis extending between said proximal end and said distal end of said catheter, a layer of stranded fibers having a plurality of fibers that extend between said proximal end and said distal end of said catheter over said core, and an electrically non-conductive layer disposed over said layer of stranded fibers thereby preventing a flow of electrical current in a radial direction through said electrically non-conductive layer, wherein said layer of stranded fibers comprises a plurality of electrically conductive wires that are connected to said electro-cautery power unit and extend to a most distal end of said catheter to form an electro-cautery cutting tip at said distal end of said catheter, and said plurality of electrically conductive wires that form said electro-cautery cutting tip being brought directly into contact with tissue to be cauterized.

12. An electro-cautery device according to claim 11, wherein substantially all fibers of said layer of stranded fibers are electrically conductive wires having electrically insulating outer layers that electrically isolate each wire along a length of said catheter from said proximal end to said distal end, said core defines a hollow path extending between said proximal end and said distal end of said catheter such that said hollow path can accommodate at least a pacing lead threaded therethrough, said plurality of fibers extend from said proximal end to said distal end of said catheter along non-overlapping helical paths, and each said electrically conductive wire is attached to said electro-cautery power unit such that it has an electrical polarity which is opposite to an electrical polarity of each adjacent electrical wire.

13. An electro-cautery device according to claim 11, wherein said plurality of electrically conductive wires form a plurality of electrically conductive paths which are electrically isolated from each other along a length of said catheter from said proximal end to said distal end, each wire of said plurality of electrically conductive wires being attached to said electro-cautery power unit such that at least one wire of said plurality of conductive wires has a first electrical polarity which is opposite in polarity to a second electrical polarity of at least one other of said plurality of electrically conductive paths.

14. An electro-cautery device according to claim 11, further comprising:

a second layer of stranded fibers having a second plurality of fibers that extend between said proximal end and said distal end of said catheter over said core, said second layer of stranded fibers being disposed between said first mentioned layer of stranded fibers and said core; and a second electrically non-conductive layer disposed between said first-mentioned layer of stranded fibers and said second layer of stranded fibers thereby preventing flow of electrical current between said first-mentioned and said second layers of stranded fibers, wherein said first-mentioned layer of stranded fibers comprises a first plurality of electrically conductive wires attached to said electro-cautery power source at a first electrical polarity and said second layer of stranded fibers comprises a second plurality of electrically conductive wires attached to said electro-cautery power source at a second electrical polarity, said first electrical polarity being opposite in polarity to said second electrical polarity, and said first-mentioned and said second layers of stranded fibers together define an electro-cautery cutting tip at said distal end of said catheter.

* * * * *